United States Patent
Bristow et al.

(10) Patent No.: US 6,972,342 B1
(45) Date of Patent: Dec. 6, 2005

(54) METHOD FOR PRODUCING CRYSTALLINE CARBOXYLIC ACIDS

(75) Inventors: Mark Anthony Bristow, Co. Durham (GB); Richard Paul Dean, Yarm (GB)

(73) Assignee: Invista North America S.A R.L., Wilmington, DE (US)

( * ) Notice: Subject to any disclaimer, the term of this patent is extended or adjusted under 35 U.S.C. 154(b) by 0 days.

(21) Appl. No.: 09/403,339

(22) PCT Filed: Apr. 8, 1998

(86) PCT No.: PCT/US98/07181

§ 371 (c)(1),
(2), (4) Date: Oct. 19, 1999

(87) PCT Pub. No.: WO98/45238

PCT Pub. Date: Oct. 15, 1998

(30) Foreign Application Priority Data

| Apr. 10, 1997 | (GB) | 9707274 |
| Sep. 10, 1997 | (GB) | 9719123 |

(51) Int. Cl.⁷ .......................................... C07C 51/42
(52) U.S. Cl. .................................................. 562/485
(58) Field of Search .............................. 562/409, 494, 562/414, 485; 422/245.1, 251; 34/373

(56) References Cited

U.S. PATENT DOCUMENTS

| 654,093 | A | * | 7/1900 | Emerick ........................ 34/91 |
| 3,629,328 | A | * | 12/1971 | Stautzenberger et al. |
| 3,661,330 | A | * | 5/1972 | Yamada et al. |
| 4,231,991 | A | * | 11/1980 | Muller et al. |
| 4,603,220 | A | * | 7/1986 | Feld |
| 6,113,866 | A | * | 9/2000 | Lee et al. |

FOREIGN PATENT DOCUMENTS

| DE | GB-2024810 | * | 1/1980 |
| GB | 2024810 A | * | 1/1980 |
| NL | 7011482 | * | 12/1970 |

* cited by examiner

Primary Examiner—Paul A. Zucker
(74) Attorney, Agent, or Firm—Charles E. Krukiel

(57) ABSTRACT

Improved process for producing purified aromatic carboxylic acid in the form of dried crystals which comprises cooling the crystals in a fluidized state after the drying step to a temperature at or below 100° C. prior to packaging and an apparatus therefor.

8 Claims, 3 Drawing Sheets

METHOD FOR PRODUCING CRYSTALLINE CARBOXYLIC ACIDS

This application claims benefit of GB Application No. 9719123.3, filed Sep. 10, 1997 and GB Application No. 9707274.8, filed Apr. 10, 1997.

BACKGROUND OF THE INVENTION

This invention relates to the packaging and/or containerization of products, and, in particular, to the conditioning of products which are in the form of crystals prior to packaging thereof.

The invention has particular application to the production of purified aromatic carboxylic acids of the type which are typically produced by liquid phase oxidation of a corresponding precursor resulting in a crude aromatic carboxylic acid which is then subjected to purification followed by crystallization from a solvent. Typical examples of such aromatic carboxylic acids and those to which this invention is most applicable are terephthalic acid, isophthalic acid, trimellitic acid, and 2,6-naphthalene dicarboxylic acid.

The purified product is recovered from a solvent by crystallization and is in the form of a filter cake. The filter cake is usually washed and then subjected to drying by the application of heat followed by storage of the recovered pure acid crystals. The product is generally produced on a continuous basis. A typical plant for commercial production of terephthalic acid, by way of example, can produce in the range of from 300,000 to 800,000 metric tons of product annually, and corresponding storage facilities, e.g., silos, for such large amounts of hot product are therefore needed in order to hold the product pending transfer into packaging bags, bulk shipping containers and the like. The product leaving the dryer is usually at a temperature well in excess of 100° C., e.g. 115° C. up to as high as 180° C., and it ordinarily undergoes natural cooling in the silo storage facility before being transferred to packaging facilities or to bulk containers.

A conventional manufacturing plant for producing terephthalic acid, for example, typically requires one or more large capacity silo storage facilities to handle the substantial throughput of product, and this, in turn, requires substantial capital investment with corresponding ongoing maintenance costs. In particular, the cost of silo storage tends to be much greater than the cost for warehouse storage of the packaged product. However, while there is an apparent incentive to reduce silo storage by shortening silo residence time, which can be achieved by simply packaging and moving the product to warehouse storage sooner rather than later, shorter residence times in the silo, and correspondingly shorter cooling times, can lead to adhesion of the acid crystals to the interior surfaces of packages/containers and rail cars, which ordinarily are unlined, along with formation of lumps in the bulk crystalline material with consequent discharge and processing problems for downstream users/consumers of the product. An effect observed when loading acid crystals at relatively high temperatures into containers which are lined, e.g., as with a polyethylene liner, is that an elevated temperature may cause the liner to soften or even fail, which leads to product contamination.

SUMMARY OF THE INVENTION

The present invention is an improved process for producing an aromatic carboxylic acid, and particularly a carboxylic acid selected from the group consisting of terephthalic acid, isophthalic acid, trimellitic acid, and 2,6-naphthalene dicarboxylic acid which comprises (i) producing a crude aromatic carboxylic acid by liquid phase oxidation of a precursor of the said aromatic carboxylic acid in an aliphatic carboxylic acid solvent; (ii) recovering the crude aromatic carboxylic acid oxidation product, and dissolving said oxidation product in water; (iii) purifying the dissolved oxidation product, and recovering the purified product from solution in the form of crystals; (iv) drying the purified crystals at an elevated temperature in the range of from 100° C. up to 180° C.; and (v) transferring the dried crystals to a silo for storage, the improvement comprising cooling the purified crystals in a fluidized state to a temperature below about 100° C., and preferably below 80° C., prior to, while or after transferring said purified crystals to said silo.

According to one embodiment of the invention, the improvement comprises dispersing the purified acid crystals in a fluidized state within a cooling zone having a coolant circulating through the cooling zone whereby heat is conveyed from the dispersed purified crystals to the coolant and removed from the cooling zone. The purified acid crystals are normally dispersed in a fluidized state as they are being transferred pneumatically from the dryer to the silo. Thus, cooling of the purified acid crystals can be achieved on a continuous basis during the transfer process.

Alternatively, the hot purified acid crystals can be conveyed directly from the dryer into the storage silo, and then cooling can be achieved according to the invention downstream of the silo as the purified crystals are being loaded batch-wise into containers. A predetermined weight, i.e., batch, of relatively hot material to be packaged is first fed from the silo into a holding vessel. Cooling can be accomplished solely by fluidizing the material within the holding vessel for a predetermined residence time, or with assistance from one or more heat exchangers deployed within the holding vessel for contacting the fluidized material. The cooled acid crystalline material is then discharged into the awaiting container, and the process is repeated.

According to another embodiment of the invention, the cooling zone is elongated and arranged vertically, and the purified acid crystals are fluidized by a moving stream of gas, e.g., air or an inert gas such as nitrogen or other inert gas, capable of moving the crystals continuously through the cooling zone. The arrangement is such that the purified acid crystals are transported upwardly through the cooling zone in a well-mixed manner typical of fluidized beds. Near the top of the tower the purified crystals, now cooled to a temperature at or below 100° C., but preferably below about 80° C., will overflow into the outlet for transfer to the silo. According to one aspect of the invention, the cross-sectional area of the tower increases along its length from the inlet to the outlet to maintain the upward gas velocity within the desired range for transporting the fluidized mass of purified acid crystals as the pressure of the gas declines and its volume increases.

The outlet of the cooling zone is preferably located above the inlet to the silo whereby the flow of the purified crystals into the silo, typically as a dried bulk material, is partially assisted by gravity. In addition, by designing the vertically elongated cooling zone with a large height to cross-sectional area ratio, the volume of fluidizing gas required to develop a fluidized bed of purified crystals can be relatively small, and, therefore, more economical to operate.

According to another aspect of the invention, there is provided an apparatus for cooling purified crystals of an aromatic carboxylic acid or other similar crystalline material from an initial temperature in the range of from 100° C. to 180° C. to a final temperature in the range of from 50° C. to 100° C. which comprises a generally elongated vessel having:

(i) at least one inlet for receiving said purified crystals;
(ii) at least one outlet for discharging said purified crystals;
(iii) at least one cooling zone positioned internally within said vessel between said inlet and said outlet; and
(iv) means for moving a supply of inert gas through said vessel at a velocity sufficient to fluidize said purified acid crystals and move them through said at least one cooling zone from said at least one inlet to said at least one outlet whereby the velocity of the gas stream is maintained within a desired range effective for transporting the fluidized mass of purified acid crystals.

Cooling of the moving stream of fluidized acid crystals is conveniently and economically accomplished while the bulk material is in motion, e.g., during transfer of the purified acid crystals from the dryer to the storage silo, by pneumatically conveying the bulk material through at least one cooling zone having a coolant medium circulating therethrough. The coolant medium, which can be process water or any other suitable liquid medium, may be introduced into the cooling zone by passing it through one or more heat transfer tubes positioned in the cooling zone so that the fluidized bulk material traverses the tubes as it passes through the cooling zone. The now heated coolant leaving the cooling zone can be used in another part of the process, such as in the case of process water, for example, for washing the purified acid crystals following their recovery from solution following the purification process. The transfer of heat to the coolant medium makes possible the use of that transferred heat in other parts of the process, which, in turn, can be translated to a reduction in the overall cost in operating the aromatic carboxylic acid production process.

DETAILED DESCRIPTION

Figure 1:
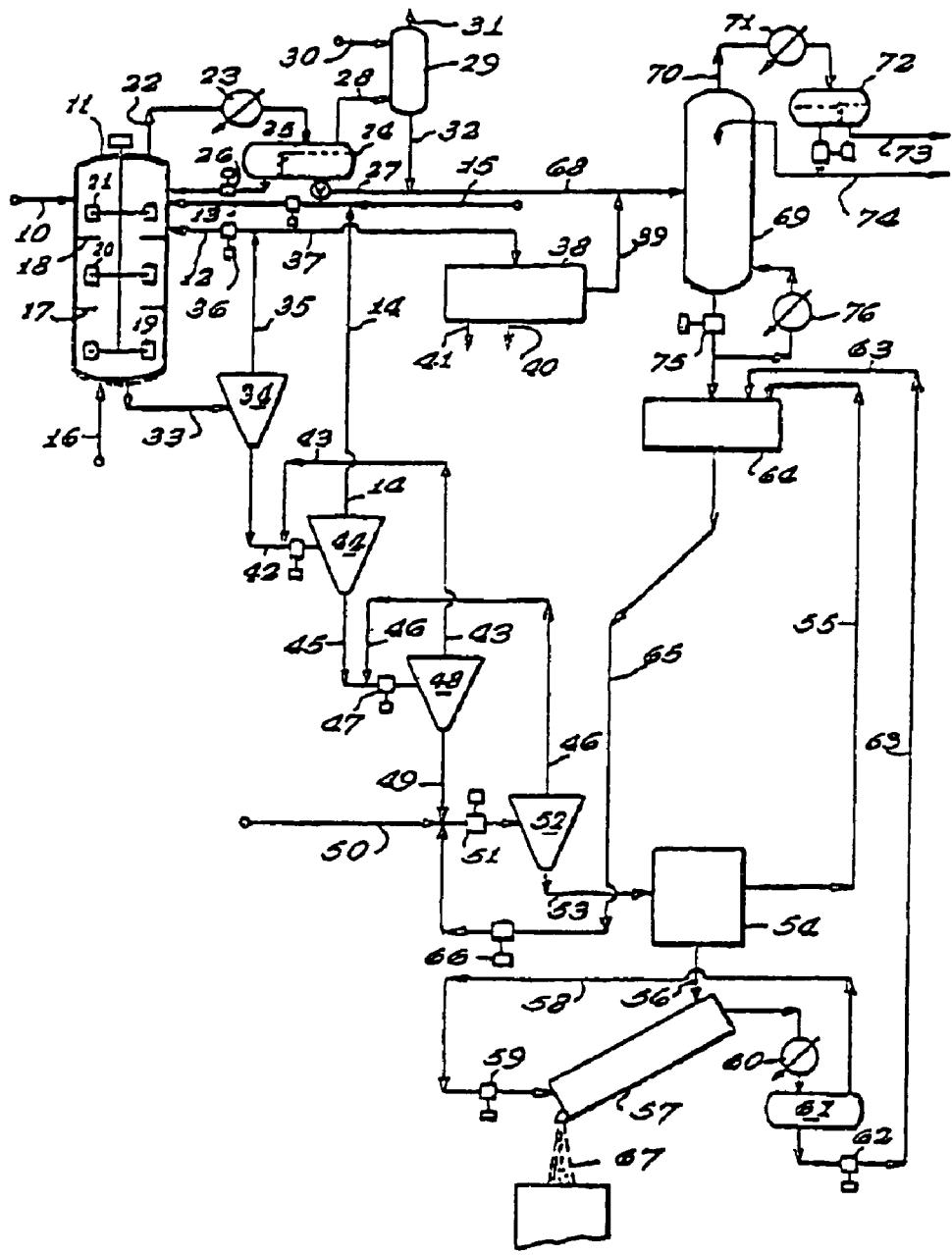
FIG. 1 is a schematic elevation view of an apparatus, i.e., vessel, for cooling purified crystals of an aromatic carboxylic acid according to one embodiment of the invention.

The present invention according to one aspect is an improved process for producing aromatic carboxylic acids, and particularly purified terephthalic acid. Using purified terephthalic acid production to illustrate the invention, in a typical commercial process, p-xylene is oxidized under elevated temperature and pressure conditions in a liquid phase reaction using air or another source of oxygen, and the oxidation is carried out in a reaction solvent comprising a C2–C6 aliphatic carboxylic acid, but usually in commercial operations acetic acid, in the presence of a catalyst system comprising one or more heavy metal compounds and one or more promoter compounds, e.g. bromine or bromine containing compound(s). Water is present in the reaction solvent and is formed as a result of the oxidation reaction. One published oxidation process suitable for producing terephthalic acid on a commercial scale can be found in European Patent No. 502628, the entire contents of which are incorporated herein by reference.

The oxidation process results in a crude terephthalic acid having as primary contaminants 4 carboxybenzaldehyde and various color bodies. In order to purify the crude acid for use in polyester polymer production, the crude acid is first dissolved in water to form an aqueous solution which is then hydrogenated at elevated pressure and temperature. The hydrogenation process chemically reduces impurities, i.e., 4-carboxybenzaldehyde is converted to paratoluic acid and by appropriate control of the recovery method, such as, for example, by crystallization of the aqueous mother liquor, so as to take advantage of the higher solubility of paratoluic acid, a high grade terephthalic acid product can be isolated. The purified acid product is recovered in the form of a filter cake from the aqueous mother liquor by a suitable solids-liquid separation technique, dried, for example, in a rotary tube dryer, and then conveyed to a silo for storage. The drying stage is accomplished using heat, and the temperature of the dried purified product exiting the dryer is typically of the order of 125° C., although the temperature can range as high as 180° C. Ultimately the product is transferred from the silo to suitable bulk containers for intermediate storage or to tank cars and trucks for direct transport to the end user. The shipping/storage container can take various forms such as a tanker vehicle for transport by road, an ISO container for shipment by sea, usually after an intermediate storage period in warehousing, a railcar or silo car, and large bags which are stored in warehouses preliminary to being transported to an end user/consumer. The ISO container and bag forms of storage can be lined with a protective polyethylene liner.

If the product is packaged after only a relatively short-term silo storage period, which is the preferred operating procedure consistent with maintaining a reduced inventory of product in silo storage at the plant site, the material is prone to adhere to the internal surface of any unlined bulk container. Bulk containers of the type described herein for handling purified acid crystals are typically made of 316 or 304L stainless steel, aluminum, or an equivalent material which resists corrosion. 304L is the preferred material of construction based on cost and corrosion resistance. In addition to surface adherence, undesirable lump formation has been observed in the product which creates handling problems.

The presence of residual moisture in the dried product is believed to be the source of these problems. Inevitably the drying process does not remove all moisture present in the purified crystals. Typically, purified terephthalic acid crystals obtained from the exit of a commercial dryer inherently contain about 0.08 to 0.12 wt % moisture. Moisture content of the "dry" acid crystals may also vary according to environmental and processing factors, such as ambient humidity in the processing area, degree of ventilation and the effects of bringing the material into contact with conveying gas which may also contain some moisture in normal operations. If moisture-containing product while still relatively hot, e.g., having a temperature of about 100° C. or higher, is loaded into a container, such as an ISO container, bulk transport or railcar which, in turn, is in thermal equilibrium with its surroundings, i.e. at or near ambient temperature, a temperature gradient typically develops through the bulk material, and this gradient results in evaporative loss of water in the hotter regions and condensation in the cooler regions of the bulk product mass. Thus, some of the bulk material is very dry while some is relatively wet which, in turn, can lead to lump formation and to adhesion of relatively damp material to the internal container surfaces due to the cohesive properties of water.

Although the foregoing investigations suggest that the problems described above could be solved by exerting greater control over the level of moisture content in the product obtained from the dryer coupled with control over moisture ingress from other sources and the use of low friction lining material for the various shipping and storage containers, such as PTFE or polyethylene liners, the cost to adopt these expedients would outweigh any advantages of economy achieved by reducing silo storage capacity and corresponding capital investment.

As defined above, the present invention is an improved process for producing an aromatic carboxylic acid in the form of purified crystals, particularly an acid selected from the group consisting of terephthalic acid, isophthalic acid, trimellitic acid, and 2,6-naphthalene dicarboxylic acid, wherein the improvement comprises cooling the purified crystals in a fluidized state to a temperature below about 100° C., and preferably below 80° C., prior to, while or after transferring the purified crystals from the dryer, where the dried acid crystals exit typically at a temperature of from 100° C. up to as high as 180° C., to the storage silo. According to the invention, purified carboxylic acid crystals cooled to at least 100° C. or below, either upon exiting the dryer or after intermediate storage in the silo, can be packed out from the storage silo sooner, meaning that the size of the silo can be reduced with a corresponding savings in initial capital investment.

According to one embodiment of the invention, the improvement comprises dispersing the purified crystals in a fluidized state within a cooling zone having a coolant, such as water, circulating through the cooling zone whereby heat is conveyed from the relatively hot dispersed purified crystals to the coolant and removed from the cooling zone. The purified acid crystals are normally dispersed in a fluidized state as they are being transferred pneumatically from the dryer to the silo. Thus, cooling of the purified acid crystals can be achieved on a continuous basis during the transfer process. The mass of hot, "dry" crystals which exits the dryer is fluidized by an inert gas stream, and the fluidized mass is moved pneumatically by the gas stream through a cooling zone and cooled on its way to the storage silo. The cost to install and operate a cooling apparatus on a commercial scale according to the invention, where heat can be transferred to a cooling medium, such as water or other process liquid, and reused somewhere else in the production process is less than the cost incurred in simply increasing the size of or the temperature of the dryer.

Alternatively, the hot purified acid crystals can be conveyed directly from the dryer into the storage silo, and then cooling can be achieved according to the invention downstream of the silo as the purified crystals are being loaded batch-wise into containers. A predetermined weight, i.e., batch, of relatively hot material to be packaged is first fed from the silo into a holding vessel. Cooling can be accomplished solely by fluidizing the material within the holding vessel for a predetermined residence time, or with assistance from one or more heat exchangers deployed within the holding vessel for contacting the fluidized material. The cooled acid crystalline material is then discharged into the awaiting container, and the process is repeated.

According to another embodiment of the invention, the cooling zone is positioned internally within a generally elongated vessel, and the vessel is arranged vertically. The purified crystals are introduced into the vessel at a location below or into the lower section of the cooling zone and fluidized by an inert gas capable of moving the crystals continuously through the cooling zone. The cross sectional area of the vessel, i.e., the cooling zone(s), may increase from the bottom to the top of the vessel such that the upward velocity of the fluidizing gas stream is maintained within a defined range as the gas pressure falls and the volume of the gas increases moving through the vessel, or tower. The arrangement is such that the purified crystals are transported through the cooling zone in a fluidized state, and near the top of the cooling zone the purified crystals, now cooled to at or below 100° C., overflow into the outlet for transfer to the silo. The outlet is preferably located above the inlet to the storage silo whereby the flow of the purified crystals, typically as a dried bulk material, into the silo is partially assisted by gravity. In addition, by designing the vertically elongated vessel which contains the cooling zone with a large height to cross-sectional area ratio, the mass of fluidizing gas required to develop a fluidized bed of purified crystals and move them through the cooling zone can be relatively small and more economical to operate than with an alternative design.

According to another aspect of the invention, there is provided an apparatus for cooling purified crystals of, for example, an aromatic carboxylic acid from an initial temperature in the range of from 100° C. to 180° C. to a final temperature in the range of from 50° C. to 100° C. which comprises a generally elongated vessel arranged vertically having:

(i) at least one inlet for receiving said purified crystals;
(ii) at least one outlet for discharging said purified crystals;
(iii) at least one cooling zone positioned within said vessel between said inlet and said outlet; and
(iv) means for moving a supply of inert gas through said vessel at a velocity sufficient to fluidize said purified crystals and move them through said at least one cooling zone from said at least one inlet to said at least one outlet whereby the velocity of said gas stream is maintained within a desired range effective for transporting the fluidized mass of purified acid crystals.

Referring now to the drawings, FIG. 1 is a schematic elevation view of an apparatus, i.e., a vessel, for cooling purified crystals of an aromatic carboxylic acid according to one embodiment of the invention for effecting upstream cooling of the purified acid crystals received from the dryer (not shown). The hot dried crystals are conveyed via line 10 into vessel 12. Vessel 12 defines a cooling zone having heat exchange means 18 positioned at first and second locations within vessel 12 as shown. In operation, a fluidized bed of purified acid crystals is established above perforated distribution grid 14 by means of an incoming flow of gas, e.g., air or an inert gas such as nitrogen, through a gas inlet nozzle 16. Heat exchange means 18, which can be a tube-type or plate type heat exchanger having water or other suitable liquid circulating therethrough as a cooling medium, are positioned so as to be immersed within the fluidized bed of moving acid crystals whereby heat is extracted from the moving mass of acid crystals as they progress upwardly through vessel. In this manner, the moving fluidized mass of purified acid crystals, as a bulk product, is cooled to a temperature on the order of from 50° C. to about 100° C., and preferably about 65° C. In the embodiment shown in FIG. 1, fluidizing gas is exhausted through line 24. Cooled acid crystals exit the cooling zone and the region of fluidization through line 25 in route to storage in the silo (not shown). Coarse crystalline material and lumps can be discharged through line 25A for separate handling. Fluidizing gas exhausted via line 24 may be used for effecting pneumatic conveyance of the cooled acid crystals exiting from vessel 12 to the silo. Because the purified acid crystalline product is cooled before being moved/conveyed to the silo for storage, the product subsequently packaged from the silo into containers and bags is free from problems associated with moisture migration in the package.

The apparatus according to the invention can be constructed from any suitable materials which are structurally acceptable and which will not cause contamination of the purified product, e.g., such as from corrosion. Stainless steels, such as 316 and 304 stainless steels, and aluminum can be used in fabrication.

Figure 2:
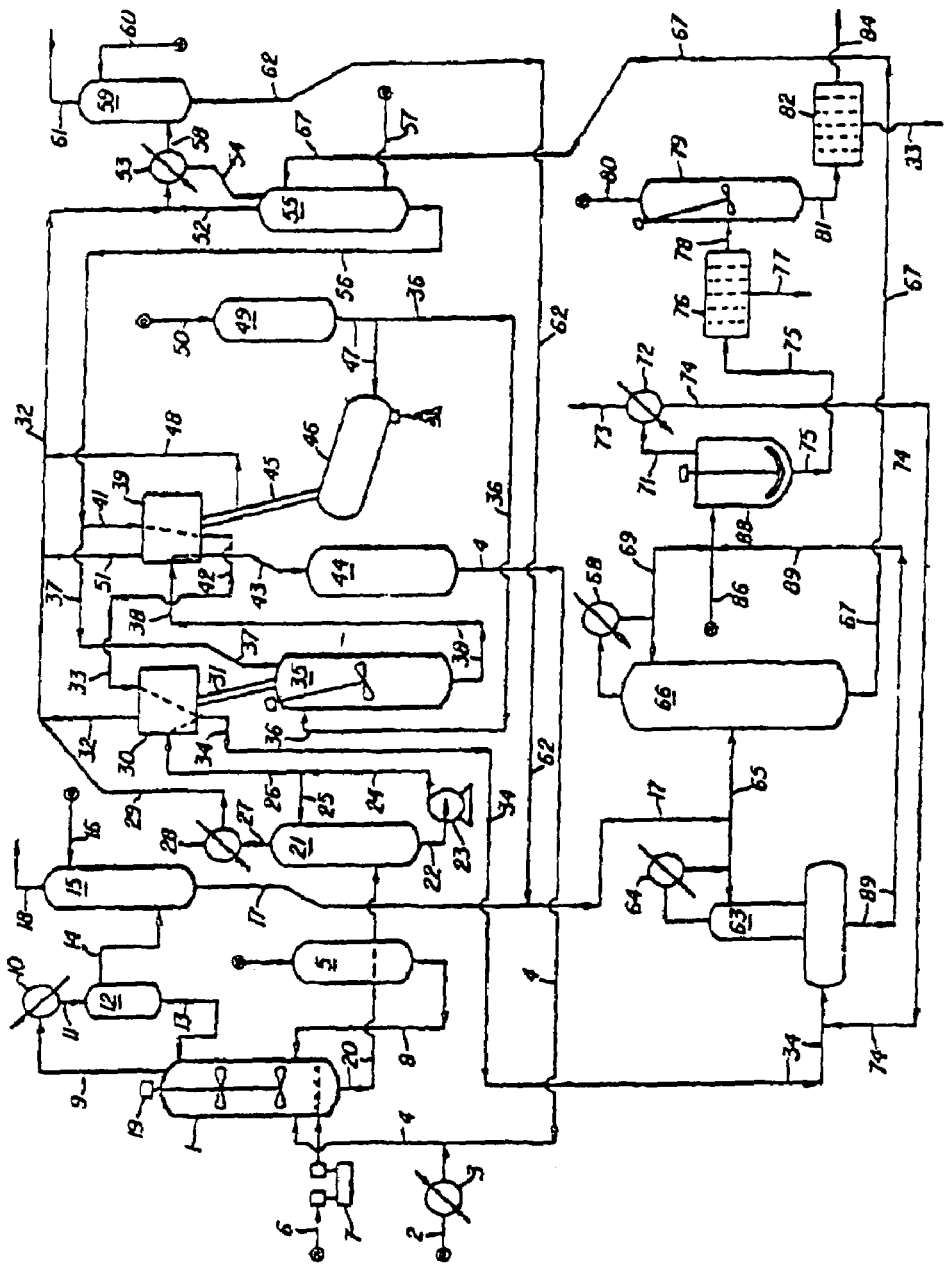
FIG. 2 is a schematic elevation view of an alternative embodiment of the apparatus shown in FIG. 1.

Referring now to FIG. 2, according to this embodiment cooling vessel 40 is elongated and takes the form of a tower, the height of which corresponds to the height of a silo which will receive cooled product from the tower. This feature takes advantage of economy and ease of operation. In practice, an apparatus according to the invention suitable for use within a production facility having a capacity to produce around 700,000 metric tons of purified carboxylic acid crystals per annum will typically have a height on the order of 20 meters, a diameter near the inlet of 0.75 meters, a diameter near the top, or discharge end, of 1.18 meters, and a heat transfer within the cooling zone of about 340 m$^2$. Means selected for moving a supply of inert gas through the tower should be capable of producing and maintaining a gas velocity of around 0.25 m/sec with a corresponding gas flow rate of 1800 kg/hr. Pressure drop for a tower meeting these specification has been measure to be about 0.0786 bar/meter (78 kPa/meter) of fluidized powder, which equates to 1.75 bar (175 kPa) over the tower as a whole. Height and diameter will, of course, depend on desired plant throughput.

Hot particulate purified acid crystals emerging from the dryer (not shown) are conveyed pneumatically by a moving stream of gas (e.g., air, nitrogen or other gas which is non-reactive with the purified acid crystals) into tower 40 through inlet 42 near the tower base. By virtue of the fluidizing effect of the conveying gas, the crystals form a rising fluidized bed within tower 40, the free upper surface of the fluidized bed being depicted by reference 44. As the product stream flows upwardly through the tower 40, it traverses a series of cooling sections 46 as shown which are formed by passage of coolant, e.g., water, through heat exchange tubes or plates. At the free surface of the fluidized bed 44, the cooled particulate crystals overflow into one or more outlets 48 so as to discharge from the tower under gravity. Each such outlet nozzle 48 may be connected with a respective storage silo so that the cooled acid crystal product will discharge into the respective silos under gravity.

A key feature of the embodiment shown in FIG. 2 is its relative height which allows for the cooled product to be discharged under gravity into adjacent storage silo(s) of comparable height. Tower 40 may be of stepped diameter from a smaller cross-sectional area near an inlet nozzle 42 to a larger cross-sectional area near an outlet nozzle 48 such that velocity of the moving fluidizing gas stream is maintained at a certain minimum value in the different regions of the tower as the gas volume increases due to the reduction of pressure up the tower. The pressure of the moving gas stream will decrease gradually according to a gradient in the vertically upwards direction. The gradient depends on factors such as vessel diameter, number of cooling zones, vessel height, product volume, etc., and can be calculated according to methods known in the art. A declining gradient accounts for a reduction of gas pressure near the top of tower 40 where the volume of gas is larger with a corresponding to a larger cross-sectional area. A reduced gas velocity and pressure in the appropriate region near the top of tower 40, referring to the volume 44A above the free surface of the fluidized bed indicated as 44, effectively controls or avoids loss of fines which tend to become entrained in the gas stream being exhausted via gas outlet nozzle 50. By increasing tower diameter with height as shown, it is possible to maintain fluidizing gas velocity at an optimum value throughout tower 40 which is suitable for fluidization/lift throughout the height of the fluidized bed. A further advantage with this configuration is that it allows for a correspondingly lower gas flow rate than would otherwise be required for a given volume of product to be conveyed.

The height of a tower 40 is normally determined by the height of storage silos, while the volume of a tower 40 is determined by the cooling surface area needed for the flow rate of hot crystallized material to be handled. To achieve a required cooling duty (i.e., to have the same internal volume to accommodate the required length of cooling tubes), a generally cylindrical tower of uniform diameter along its height would have to be larger at the bottom of the cylinder as compared with a tower whose diameter increases with height. A larger diameter at the bottom of the tower, in turn, would necessarily require a higher gas flow rate to achieve the needed fluidization velocity at the bottom of the vessel.

Figure 3:
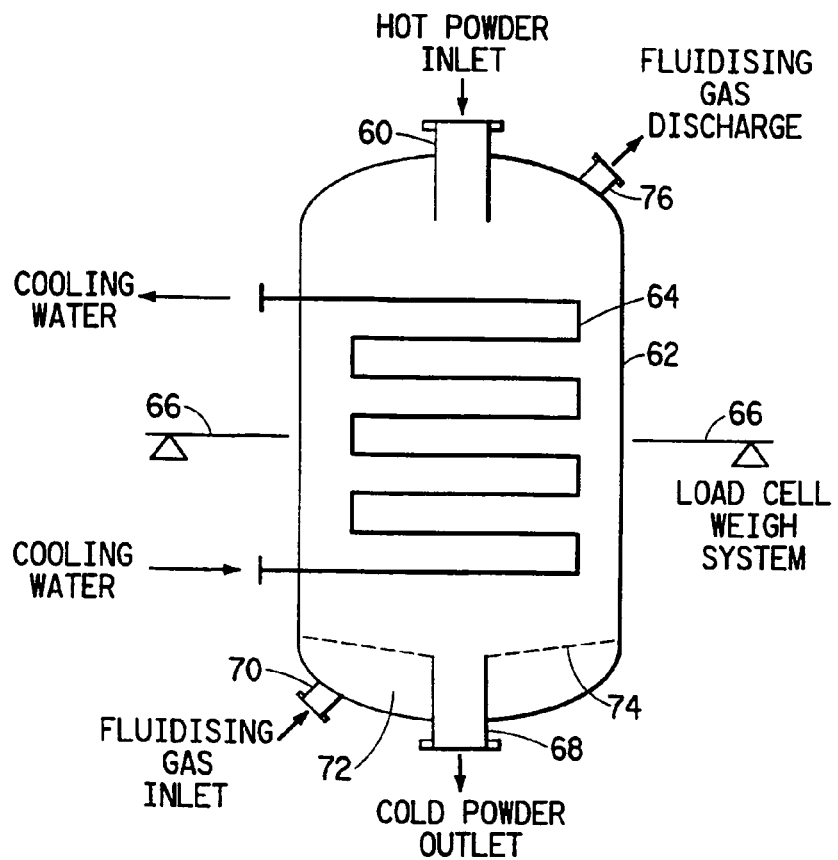
FIG. 3 is a schematic elevation view of an apparatus according to the invention for batch-wise handling and cooling of purified acid crystals.

In the embodiments shown in FIGS. 1 and 2, the purified acid crystals are force cooled upstream of the storage silo. However, forced cooling according to the invention may also be effected downstream of the storage silo as shown in FIG. 3. In this embodiment, hot purified acid crystals for transport or packaging can be transferred batch-wise from the storage silo through inlet nozzle 60 into vessel 62 which is equipped with a heat exchanger 64 of suitable size/surface area. Vessel 62 is mounted on a load cell weighing system 66 so that predetermined weights of material can be conveyed into and through vessel 62 for packaging or loading into vehicles, as the case may be. In operation, hot purified acid crystals are discharged from the storage silo into vessel 62 through inlet nozzle 60 and held therein until the desired temperature is attained, at which time the now cooled crystal product is released through outlet nozzle 68 (which may be provided with a suitable control valve, not shown) into an awaiting storage container. The contents of vessel 62 may be fluidized during batch residence time using, for example, air or nitrogen as the fluidizing gas medium. Inert fluidizing gas is supplied through gas inlet nozzle 70 into chamber 72 defined as the volume within the vessel bottom and a perforated distribution plate 74 through which the fluidizing gas enters and fluidizes the mass of crystalline material in the vessel. The fluidizing gas exits the vessel 62 via gas discharge nozzle 76. The fluidizing gas may effect cooling of the crystalline mass to supplement the cooling effect of the heat exchanger 64, although the fluidizing gas may be the primary or sole cooling source under some conditions.

In the embodiment shown in FIG. 3, holding vessel 62 is sized to suit the largest container unit to be filled (i.e., ISO container, road tanker, etc.) A corresponding weight of material to be packaged and shipped would then be fed into vessel 62 from the silo through inlet nozzle 60. It would be held momentarily as it is cooled via fluidization by the moving stream of gas, and then discharged directly into the awaiting container or tanker for dispatch.

Mounting vessel 62 on load cells 66 for batch weighing is optional, although preferable over any other type of weighing system for accurate control of material being packed out.

Figure 4:
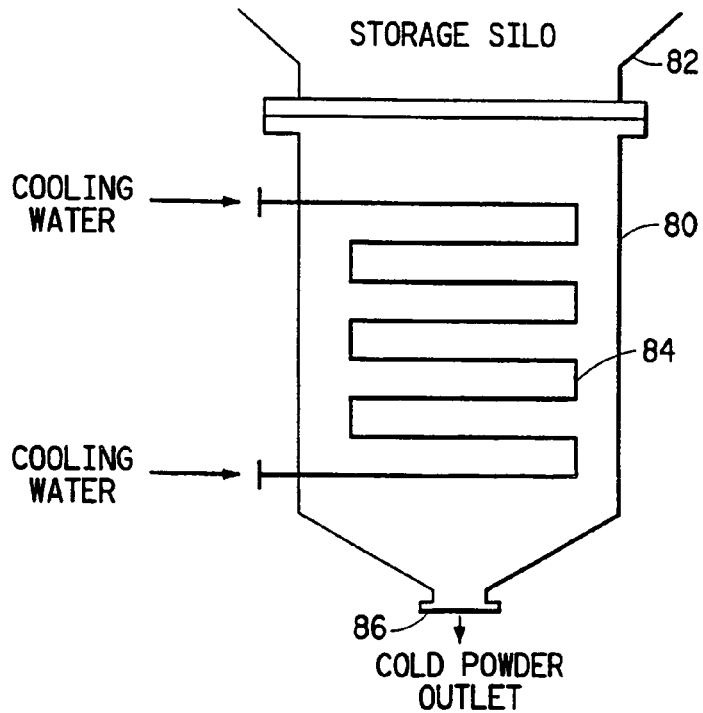
FIG. 4. is a schematic elevation view of an apparatus according to the invention shown deployed downstream of the storage silo.

FIG. 4 illustrates a variation of the embodiment shown in FIG. 3 where cooling vessel 80 is mounted directly to the discharge outlet of a storage silo 82. Coolant is circulated through heat exchanger coil 84. Fluidizing gas may be provided to assist discharge of the cooled acid crystals through outlet 86. In this embodiment, cooling vessel 80 is filled as an integral part of storage silo 82, and cooling may therefore be carried out at any time, if needed, prior to discharging the purified acid crystals into containers.

In each of the illustrated embodiments the coolant, either pure of process water, solvent, etc., is suitable for recycling for use in some other part of the production process for the aromatic carboxylic acid. In the case of producing purified terephthalic acid, for example, if the coolant is water, it can be recycled for use in washing the crystallized product after recover from crystallization, or used in dissolving crude terephthalic acid prior to purification. Both of these water recycle alternatives make use of the heat recovered from cooling the purified terephthalic acid crystals according to the invention.

What is claimed is:

1. An improved process for producing a purified aromatic carboxylic acid which comprises:
   (i) producing a crude aromatic carboxylic acid by liquid phase oxidation of a precursor of said aromatic carboxylic acid in an aliphatic carboxylic acid solvent;
   (ii) recovering the crude aromatic carboxylic acid oxidation product, and dissolving said oxidation product in water;
   (iii) purifying the dissolved oxidation product, and recovering the purified product from the aqueous solution in the form of crystals;
   (iv) drying the purified crystals at an elevated temperature in the range of from about 100° C. up to about 180° C.; and
   (v) transferring the dried crystals to a silo for storage, the improvement comprising cooling the purified acid crystals in a fluidized state with a cooling means to a temperature below about 100° C. prior to, while or after transferring said purified crystals to said silo;
   wherein the cooling means comprises at least one heat exchanger deployed within a holding vessel, and wherein the at least one heat exchanger is selected from the group consisting of: a tube-type heat exchanger and a plate-type heat exchanger.

2. The process according to claim 1, in which the heat exchanger comprises water circulating therethrough.

3. The improved process according to claim 1, in which the crystals are cooled to a temperature of about 65° C. or less.

4. An improved process for producing a purified aromatic carboxylic acid which comprises:
   (i) producing a crude aromatic carboxylic add by liquid phase oxidation of a precursor of said aromatic carboxylic acid in an aliphatic carboxylic acid solvent;
   (ii) recovering the crude aromatic carboxylic acid oxidation product, and dissolving said oxidation product in water;
   (iii) purifying the dissolved oxidation product, and recovering the purified product from the aqueous solution in the form of crystals;
   (iv) dying the purified crystals at an elevated temperature in the range of from about 100° C. up to about 180° C.; and
   (v) transferring the dried crystals to a silo for storage, the improvement comprising cooling the purified acid crystals in a fluidized state with a
   cooling means to a temperature below about 100° C. prior to, while or after transferring said purified crystals to said silo;
   wherein the cooling means comprises a cooling zone that is positioned internally within an elongated vessel having an inlet and an outlet for the purified acid crystals, wherein the vessel is arranged vertically and wherein the cross-sectional area of the vessel increases along its length from a first value in the region of the inlet to a final value in the region of the outlet.

5. The improved process according to claim 4, wherein the cooling zone has a coolant circulating through the cooling zone whereby heat is conveyed from the purified crystals to the coolant and removed from the cooling zone simultaneously as the purified acid crystals are cooled.

6. The improved process according to claim 5, wherein the purified acid crystals are discharged from the dryer and dispersed into a fluidized state by a moving stream of inert gas, and the fluidized crystals are moved continuously through the cooling zone from the inlet to the outlet and discharged into the silo.

7. The improved process according to claim 6, in which the inert gas is selected from nitrogen and air, and the coolant is selected from the group consisting of solvent, process water, and pure water.

8. The improved process according to claim 4, in which the crystals are cooled to a temperature of about 65° C. or less.

* * * * *